United States Patent [19]

Pohl et al.

[11] 4,455,233

[45] Jun. 19, 1984

[54] METHOD AND APPARATUS FOR ION ANALYSIS AND DETECTION USING REVERSE MODE SUPPRESSION

[75] Inventors: Christopher A. Pohl, Hayward; Rosanne W. Slingsby, Pleasanton; Edward L. Johnson, Milpitas; Leilani Angers, Santa Clara, all of Calif.

[73] Assignee: Dionex Corporation, Sunnyvale, Calif.

[21] Appl. No.: 522,829

[22] Filed: Aug. 12, 1983

[51] Int. Cl.$^3$ ............................................. B01D 15/08
[52] U.S. Cl. .................................... 210/635; 210/656; 210/198.2; 422/70
[58] Field of Search ............ 216/635, 656, 659, 198.2; 422/70

[56] References Cited

U.S. PATENT DOCUMENTS

| | | | |
|---|---|---|---|
| 3,598,728 | 8/1971 | Bixler et al. | 210/635 |
| 4,265,634 | 5/1981 | Pohl | 210/656 X |
| 4,314,823 | 2/1982 | Rich, Jr. et al. | 210/656 X |
| 4,403,039 | 9/1983 | Ban et al. | 210/656 X |

*Primary Examiner*—John Adee
*Attorney, Agent, or Firm*—Flehr, Hohbach, Test, Albritton & Herbert

[57] ABSTRACT a method of ion analysis and detection of weakly dissociated anions or cations in an eluent by first separating such ions on a chromatographic separation medium by ion exclusion chromatography or mobile phase ion exclusion chromatography. The eluent include an acid or base with a co-ion of the same charge as the ions to be separated, such co-ions being in the hydronium or hydroxide form. In one embodiment the effluent from the separation medium is contacted with one side of an ion-exchange membrane having exchangeable ions of opposite charge to the ionic species. The opposite side of the membrane includes a regenerant with salt-forming suppression ions capable of forming a weakly conducting salt with the co-ions. Then the separated ionic species are detected preferably by a conductivity detector. In another embodiment, the membrane is replaced by a resin bed with ion-exchanging sites of opposite charge to the co-ions. There, co-ions form a suppressed salt with the exchangeable ions.

18 Claims, 1 Drawing Figure

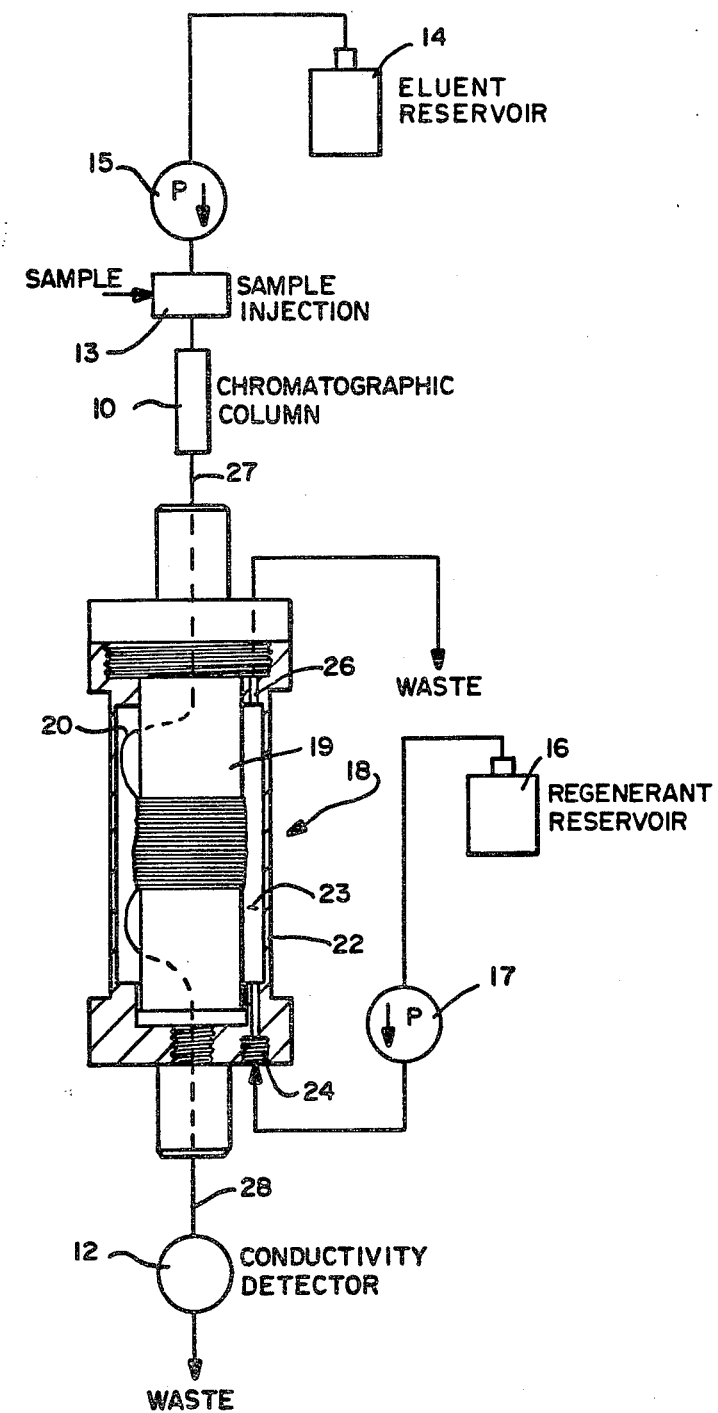
FIG.—1

METHOD AND APPARATUS FOR ION ANALYSIS AND DETECTION USING REVERSE MODE SUPPRESSION

BACKGROUND OF THE INVENTION

The present invention relates to separation of ions by liquid chromatography followed by ion suppression and detection.

One form of ion chromatography includes the use of two ion-exchange columns in series, followed by a flow-through detector. The first column separates the ions of injected sample by eluting of the sample through the column using an electrolyte eluent. In the second column, termed a "suppressor", the electrical conductivity of the electrolyte in the eluent, but not of the separated ionic species, is suppressed so that the ionic species can be determined by a conductivity cell. This technique is described, for example, in U.S. Pat. Nos. 3,897,213; 3,920,397; 3,925,019; and 3,926,559. The disclosures of such patents are incorporated herein by reference.

An improved form of suppressor has been developed in the form of a membrane, such as a fiber, which allows for continuous analysis of consecutive samples without periodic regeneration or replacement of the suppressor column. One such column is described in published European patent application No. 32,770, in which such a charged fiber membrane is used in place of the resin bed. The sample and eluent are passed through the fiber with a flowing regenerant at the outside wall of the fiber. The fiber comprises an ion-exchange membrane partitioning the regenerant from the effluent of chromatographic separation. The membrane passes ions of the same charge as the exchangeable ions of the membrane to convert the electrolyte of the eluent to weakly ionized form, followed by detection of the separated ions. For analysis of cations, an eluent, including a strong base electrolyte, such as sodium hydroxide, is used for separation. A dilute aqueous solution of a strong acid, such as sulfuric acid, is used as the regenerant. The ion-exchange membrane is of a form which allows sodium ion to permeate out of the fiber while hydrogen ion permeates in. In this manner, the sodium hydroxide in the eluent stream is converted to de-ionized water and the sodium ions are dispersed in the regenerant and ultimately to waste as sodium sulfate and sodium bisulfate. The cations to be analyzed are in hydroxide form and of suitable ionization for detection by a conductivity detector or the like. For anion analysis, an appropriate modification of the charges of the components are made. As used herein, the term "prior art membrane suppression" refers to a system of this general type.

Prior art membrane suppression is highly effective for suppression in a system where the ions to be analyzed are highly ionized in the acid or base form, the form in which they are passed to the detector. However, if such ions are weakly dissociated in the acid or base form, difficulties arise in the detection of the ion conductivity of such analyte ions based upon their conductivity. Thus, the system may not be effective for analyzing weakly basic (herein "weak") cations such as amines or weakly acidic (herein "weak") anions such as carboxylates.

One technique for the separation of weak anions or cations is by ion exclusion chromatography (IEC) using a medium, typically a resin bed, with permanently attached ion-exchange sites, (hereinafter "IEC"). The IEC mode of separation is described in U.S. Pat. No. 4,314,823, incorporated herein by reference. Briefly summarized, an accepted theory of separation by ion exclusion chromatography is that the resin network serves as a boundary, which behaves as a semi-permeable membrane between the interstitial liquid in the resin particles and the occluded liquid inside the resin. Due to Donnan exclusion, highly ionized molecules, such as strong mineral acids or bases, are excluded from the resin particles and pass directly through the column in the void volume peak. Weakly ionic molecules may enter the resin phase in acid or base form, depending upon the form of the ion-exchange sites, and are retained by the resin for a later elution than the strong acids. In general, referring to the separation of anions, the weak acids in their molecular substantially non-ionized form can penetrate into the interior of the ion-exchange resin while the highly ionized acids are excluded. By using ion-exchange resin in hydrogen ion form, salts of weak acids which are highly ionized (e.g. of alkali metals) are converted to their acid form which may be retained by the column. For example, sodium acetate is converted on the column to acetic acid and the sodium ion is retained by the column. Thereafter the acetic acid is resolved from other weak acids and eluted from the column in a separate peak volume which can be detected. The above dicussion of ion exclusion chromatography applies in analogous manner to the separation of cations, except, in this case, an ion-exchange resin in the hydroxide form is used in the ion exclusion column.

Another system ffr separating and analyzing ions is by substituting mobile phase ifn chromatography (MPIC) for the ion chromatography, using a resin bed suppressor. This MPIC system is described in U.S. Pat. No. 4,265,634. Here, the separation medium is a porous hydrophobic chromatographic resin with essentially no permanently attached ion-exchange sites. An ion-exchange site-forming compound, including a hydrophobic portion and an ion-exchange site, is passed through the column and forms reversible adsorptive bonds with the resin to create ion-exchange sites.

It is an object of the invention to provide a system of ion analysis combining certain prior art principles utilizing membrane suppression but which is an improvement upon prior art membrane suppression, particularly for the analysis of ions which are only weakly associated in their acid or base form.

SUMMARY OF THE INVENTION

The invention relates to an improved method and apparatus in which ions in an electrolyte eluent are chromatographically separated and the effluent is treated to suppress the electrolyte prior to detection of the ions.

The method of chromatographic separation is either IEC or a combination of IEC and MPIC (termed "MPIEC"), as applied to weak ionic species in an eluent including an electrolyte. For the analysis of anions, the electrolyte typically is an acid, and for the analysis of cations, the electrolyte typically is a base. As used herein, in the IEC mode, the term "co-ion" will refer to the anion of the acid electrolyte and the cation of the base electrolyte, the same charge as the ionic species. For MPIEC, the term "co-ion" refers to the ion of the ion-exchange site-forming compound of the same charge as the analyte ion.

In a preferred embodiment, after separation of the ionic species, the effluent is contacted with one side of an ion-exchange membrane having exchangeable ions of opposite charge to the ionic species. The membrane is permeable to ions of the same charge as the exchangeable ions and resists permeation through the membrane of ions of opposite charge. Simultaneously, the opposite side of the membrane is contacted with a regenerant. The membrane forms a permselective partition between the regenerant and the effluent. The regenerant includes salt-forming suppression ions of opposite charges to the ionic species and co-ions. The membrane is permeable to the suppression ions and to corresponding hydronium or hydroxide ions. The suppression ions are selected to be capable of forming a suppressed salt with the co-ions of substantially lower equivalent conductance than the corresponding hydronium or hydroxide form of the co-ions. The hydronium or hydroxide ions extracted from the effluent at the ion-exchange sites of the membrane are diffused through the membrane into the regenerant. The suppression ions are diffused from the regenerant into the effluent to form the suppressed salt. Then the separated ionic species are detected, preferably by a conductivity detector.

In another embodiment, an ion-exchange resin bed is utilized instead of the ion-exchange membrane to suppress the electrolyte in the eluent. In this instance, the resin includes ion-exchanging sites with exchangeable ions of opposite charge to the ionic species and to the co-ions. The exchangeable ions form suppressed salts with the co-ions of substantially lower equivalent conductance than a corresponding hydronium or hydroxide form of the co-ions. Then the separated ionic species are detected as set forth above.

BRIEF DESCRIPTION OF THE DRAWING

FIG. 1 is a schematic representation of apparatus useful in performing the present invention.

DETAILED DESCRIPTION OF THE PREFERRED EMBODIMENTS

The system of the present invention is useful for determining a large number of weak ionic species so long as the species to be determined are solely anions or solely cations. A suitable sample includes surface waters, and other liquids such as industrial chemical waste, body fluids, beverages such as fruits and wines, and drinking water. When the term "ionic species" is used herein, it includes species in ionic form and components of molecules which are ionizable under the conditions of the present system.

Referring to FIG. 1, a simplified apparatus for performing the present invention is illustrated. The system includes chromatographic separation means 10 including a chromatographic separation medium.

The chromatographic separation medium is of a type capable of separating the weakly dissociated anions or cations by ion exclusion chromatography. In the IEC embodiment, such resin includes permanently attached ion exchanging site with exchangeable ions of opposite charge to the weak ionic species so that chromatographic separation is performed by selective temporary retention on the column. In the MPIEC embodiment, the chromatographic separation medium is of a type conventionally employed for MPIC as described in detail in U.S. Pat. No. 4,265,634, even though the technique of separation is substantially different as set forth in detail below. Briefly summarized, such chromatographic separation medium includes a porous hydrophobic chromatographic medium, preferably a resin bed, with essentially no permanently attached ion-exchanging sites.

Arranged in series with column 10 is suppressor means 11 for suppressing the conductivity of the electrolyte of the eluent but not the conductivity of the separated ions.

The effluent from suppressor means 11 is directed to a detector for detecting the resolved ionic species therefrom, preferably in the form of a flow-through conductivity cell 12. A suitable sample is supplied to sample injection valve 13 which is swept through the apparatus by the solution of eluent from eluent reservoir 14 drawn by pump 15, and then passed through the sample injection valve 13. (Alternatively, the pump may be eliminated in a gravity flow system.) The solution leaving column 10 is directed to a suppressor means 11 wherein the electrolyte is converted to a weakly conducting form. The eluent with separated ionic species is then treated by suppressor means 11 and passed to conductivity cell 12.

In conductivity cell 12, the presence of ionic species produces an electrical signal proportional to the amount of ionic material. Such signal is typically directed from the cell 12 to a conductivity meter, not shown, thus permitting detection of the concentration of separated ionic species.

The suppressor means includes a reservoir or source of regenerant 16, a chromatographic pump 17, and an ion-exchange membrane device 18. Conduits are provided between the reservoir and membrane device to deliver regenerant to the latter.

A suitable membrane device is supplied by Dionex Corporation, Sunnyvale, Calif., under the designation Cation Fiber Suppressor (Part No. 35352). It includes a core 19 around which membrane fiber 20 is wound in a coil of a sufficient number of turns (e.g., 6 ft.) to provide adequate contact with the fiber walls for permeation of ions between the regenerant and eluent. A shell 22 encloses core 19 and forms therewith a regenerant passageway or chamber 23. The chamber receives regenerant through regenerant inlet 24, and the regenerant is discharged to waste through regenerant outlet 26. Column effluent flows through the fiber 20 downwardly from membrane inlet 27, through the coil and out membrane outlet 28. In operation, suppressor means 12 operates by receiving the effluent from the separating column 10, which flows through the interior of the fiber of suppressor column 18. Simultaneously, solution from reservoir 16 is pumped in a generally counterflow direction into regenerant inlet 24, and removed from regenerant outlet 26 to waste.

The system of the present invention is applicable to weak anions and weak cations. As defined herein, "weak anions" are anions which, in acid form, are ionized and have a relatively high $pK_A$ value (e.g., about 2 to 7) and which are resolved by IEC, in comparison to "strong anions" which are defined to be highly ionized in acid form, have a relatively low $pK_A$ value (e.g., 0 to about 2) and which are not resolved by IEC.

As further defined herein, "weak cations" are cations which, in base form, are poorly ionized, having a relatively high $pK_B$ value (e.g., about 2 to 7), and which are resolved by IEC in comparison to "strong cations" which are defined to be highly ionized in base form, have a relatively low $pK_B$ value (e.g., 0 to about 2), and which are not resolved by IEC.

As further defined herein, "weak ionic species" are either weak anions or cations depending upon whether or not the method is used for their separation.

Typical weak anions include mono-, di- and tricarboxylate groups (e.g., formates and acetates), carbonates, alkyl sulfonic acids, phosphonic acids, and phosphoric acids. Typical weak cations include primary, secondary, and tertiary amines, ammonia, and some quaternary amines.

IEC

A suitable ion-exchange resin bed includes a resin of a neutral macroporous type which has been functionalized by strong acid groups such as sulfonic groups or strong base groups such as quaternary amines. The neutral resins may be formed as set forth in U.S. Pat. No. 4,224,415, and sold by Dionex Corporation of Sunnyvale, Calif. for use in an MPIC - NSI column. This neutral macroporous resin is functionalized to the sulfonate form by soaking in concentrated sulfuric acid followed by aspiration and addition to water followed by filtration as described in Pohl, C. and Slingsby, R., U.S. patent application entitled "Method And Apparatus For Mobile Phase Ion Chromatography And Membrane Suppression", filed simultaneously herewith. Such resin is of the type in which the dominant retentive force is penetration of the weak acid (or base) in molecular form into the interior of the resin for retention there for a time until elution in the eluent stream in reverse order to such retention forces. This effect dominates over any ion-exchange effect. To permit this to occur, the pore size of the resin should be relatively large so that such molecules may penetrate the resin. The specific exchange capacity of the resin particles is not critical. A suitable level is on the order of about 0.1 to 5 milliequivalents per gram (meq./g.) of resin.

A major difference in the separation in accordance with the present invention and in the prior art ion exclusion chromatography using resin with permanently attached ion-exchange sites resides in the eluent. In both systems, the eluent must include an eletrolyte capable of converting weak ionic species in salt form into the suppressed or non-ionized acid or base form. Referring to the analysis of anions by conventional IEC, such electrolyte is typically a strong mineral acid, such as hydrochloric acid, while in the analysis of cations, the eluent is a strong base such as sodium hydroxide. For reasons set out below, such electrolytes would not be preferred for suppression by the techniques of the present invention. Acids or bases are still employed but the anion of the acid and the cation of the base must be of a particular type. Expressed in a different manner, the co-ions of the hydronium or hydroxide in the acids and bases, respectively, being of the same charge as the ionic species, must also be of a type capable of suppression by the present invention. For that purpose, such co-ions must be capable of forming suppressed salts with the suppression ions in a regenerant, as described below, which suppressed salt is of substantially lower equivalent conductance than the corresponding hydronium or hydroxide form of the co-ions. This is because the suppression ions of the regenerant contact the effluent stream from separation and form such suppressed salts which pass to the detector with low conductivity.

By way of example, for anion analysis in accordance with the invention, the ion-exchange resin may be a sulfonate type of resin with hydrogen ion exchangeable groups, the eluent may be a sulfonate or a carboxylate co-ion in acid form in water, and may include an appropriate organic solvent. In this instance, the suppressor ion which forms a suppressed salt with this co-ion is typically a cation such as a quaternary ammonium ion.

The preferred mode of suppression is by use of an ion-exchange membrane similar in some respects to the ion-exchange membrane described in the aforementioned published European patent publication but with a substantially different function. In accordance with the present invention, the effluent from the separation medium is passed through one side of an ion-exchange membrane, suitably by flowing through the fiber of the device shown in FIG. 1. As with the prior art membrane suppression, the ion-exchange membrane has exchangeable sites of an opposite charge to the ionic species and is permeable to ions of the same charge as the exchangeable ions. Furthermore, the membrane resist permeation of ions of opposite charge to such exchangeable ions. Simultaneously, the opposite side of the membrane is contacted with the regenerant which includes the salt-forming suppression ions of opposite charge to the ionic species and co-ions. In prior art membrane suppression for cations using a base electrolyte, such as sodium hydroxide, the sodium ions diffuse out of the fiber into the regenerant while hydrogen ions in the regenerant diffuse in the opposite direction into the effluent to form water. In contrast, in accordance with the present invention, a reverse mode of membrane suppression is employed.

For cation suppression, the electrolyte may be phosphonium and sulfonium hydroxides or, preferably, quaternary ammonium hydroxides such as TBAH. The membrane includes ion-exchange sites with exchangeable ions (i.e. methane sulfonate) of the opposite charge to the co-ion of the base electrolyte which thus resist permeation through the membrane of the co-ion, tetrabutyl ammonium ion (TBA). The hydroxide ions pass through the membrane into the flowing regenerant. Conversely, the suppression ions of the regenerant, being negatively charged, pass through the membrane and into the effluent to form a suppressed salt with the co-ions in the effluent. Preferable suppression ions for cation analysis include sulfonate ions characterized by the capability of forming weakly ionized suppressed salts with the co-ions, typically, TBAH. Typical equivalent conductances for the suppression ions are less than 200 $\mu S$ and preferably less than 50 $\mu S$. The same relationship applies for the co-ions. The regenerant stream includes an acid of the suppression ion (sulfonate). In this manner, the hydroxide ion diffusing from the effluent to the regenerant side of the membrane forms water in the regenerant side with the hydrogen ion remaining after the suppression ion (sulfonate) diffuses in the reverse direction into the effluent to form the suppressed salt in the effluent.

For anion analysis, the eluent includes an acid electrolyte with suitable co-ions of sulfonate or carboxylate form. The suppression ion is suitably a quaternary ammonium ion. The exchangeable ions of the ion-exchange membrane then comprise cations such as hydronium ion rather than anions. Viewed in another manner, the co-ion ffor anion analysis are suitable for use as the suppressor ions for cation analysis while the suppressor ions for anion analysis are suitable for use as the co-ions of cation analysis.

The theory of operation of the membrane is similar to, but in the reverse mode from, prior art membrane suppression. In both instances, ions extracted from the effluent at the active ion-exchange sites of the membrane are diffused through the membrane and are exchanged with ions of the regenerant, and thus diffuse ultimately into the regenerant. The exchangeable ions of the ion-exchange membrane are in the form necessary to convert the electrolyte of the eluent to a weakly conducting form.

Referring specifically to cation analysis according to the present invention, the membrane is typically a strong base anion exchange membrane (positively charged), preferably with quaternary ammonium functional groups, and which is typically in the hydroxide ion form. In this form, the membrane is permeable to anions but not cations. The permeating anions are captured at the active ion-exchange sites at the membrane and thus diffused through the membranes. The diffusing ions are eventually exchanged near the opposite surface of the membrane with ions from the regenerant, and thus ultimately diffuse into the regenerant, and are removed from the separator column effluent. The membrane continuously replaces the extracted anions with like charges which suppress the conductivity of the electrolyte. While the membrane is continuously being exhausted, it is simultaneously continuously regenerated by the ion-exchange reactions occurring to the interface of the regenerant in the membrane.

Ion-exchange membranes having the permselective ion transfer property set out above are known for other uses. Certain such membranes are described by R. M. Wallace, "Concentration And Separation Of Ions By Donnan Membrane Equilibrium", *I & EC Process Design and Development*, 6 (1967). As described in the aforementioned published European patent application, such membranes may be in the form a flat sheet or one or more hollow fibers. Typically, the fibers have an internal bore size less than about 1,000 microns. One suitable fiber which has been used commercially for suppression is supplied by DuPont under the trade name Nafion, and has been utilized by Dionex Corporation in its fiber suppressor devices for conventional ion chromatography.

While the above type membrane is suitable for suppression of the effluent of conventional ion chromatography, as set forth above, it may not be suitable for the present invention for a number of reasons. Firstly, the membrane must be of a type capable of passing suppressor ions which are capable of forming suppressed salts on the effluent sides of the membrane. As set forth above, for cation analysis, one preferred suppressor ion is tetrabutyl ammonium (TBA) ion, having an approximate size of 10 angstroms. (As used herein, size refers to approximate effective ionic radius in aqueous solutions at 25° C.) In contrast, it has been found that Nafion, the membrane previously used, will pass tetramethylamonium hydroxide (6 angstrom size), but not tetrapropylamonium hydroxide (8 angstrom size). Thus, for cation analysis, it is preferable to use a membrane capable of passing ions of a size greater than 6 to 8 angstroms.

A stable membrane capable of transporting ions of a size greater than 7 angstroms, and preferably greater than 10 angstroms, has been developed which is capable of transporting the TBA ion in a reasonable period of time. This renders the membrane useful for suppression since the TBA ions are transported across the membrane during use in a typical anion analysis as set out below. In one technique for forming this ion-exchange membrane, intravenous tubing introduced by hospitals is employed as a base material, such as supplied under the trade name Microline by Thermoplastic Scientifics, Inc., Warren, New Jersey. This particular membrane is a co-polymer of 91% ethylene and 9% vinyl acetate, dimensioned at 0.011 inch i.d. and 0.024 inch o.d. A monomer, suitably vinyl benzyl chloride, is grafted onto this tubing to render it suitable for conversion to ion-exchange form. Thereafter, the grafted tubing is aminated as set forth in Slingsby, R., and Pohl, C., U.S. patent application entitled "Method And Apparatus For Mobile Phase Ion Chromatography And Membrane Suppression", filed simultaneously herewith.

A suitable technique for grafting is by irradiation of the tubing in a solution of the monomer in an organic solvent such as methylene chloride. A suitable concentration of monomer and solvent ranges from 32% to 70%, and preferably 45% to 55%. An appropriate irradiation dose is 10,000 rads/hour of gamma rays at the time of 72 hours to 400 hours and a tempeature of 80° C. to 90° C. under an inert atmosphere such as nitrogen. A suitable technique for forming a sulfonated or aminated membrane is set forth in Slingsby, R. and Pohl, C., U.S. application entitled "Analysis Of Liquid Streams Using Tubing With Protuberances On Its Inner Wall", filed simultaneously herewith.

As set forth above, the co-ions form suppressed salts with the suppression ions of low ionic conductance due to a careful selection of appropriate suppression ions and co-ions. Preferably, the equivalent conductances of each ion in the suppressed salts is less than 100 $\mu$S, preferably less than 30 $\mu$S. Thus, the equivalent conductance of either the suppression ion or the co-ion may be relatively high so long as the equivalent conductance of the other ion in the suppressed salt is relatively low. In other words, the total of the equivalent conductance for the suppression ions and co-ions should be relatively low, e.g. less than 100 $\mu$S. The concentration of co-ion and suppressed ion is such that a soluble suppressed salt is formed with the regenerant cation in water or with a non-ionic surfactant in water. Appropriate use levels for this purpose are from 200 micromoles to 50 millimoles. A non-ionic surfactant may be used at levels of 0.1% to 10% (w/w) in sufficient quantities to solubilize the suppressed salt.

The regenerant system for the analysis of weak acids includes an organic or inorganic base with suppression ions (cations) of equivalent conductance also less than 100 $\mu$S and preferably less than 30 $\mu$S. The counter-ions of such cations may be hydroxide, carbonate, borate or the like.

As appropriate co-ions and suppression ions are selected on the basis of the equivalent conductance, the anion eluent or regenerant may be selected from the same grouping and include one or more of the following: $C_6$–$C_{12}$ sulfonic acids, halogenated carboxylic acids such as tridecafluoroheptanoic or nonadecafluorodecanoic acid, alkyl hydrogen sulfates such as dodecyl hydrogen sulfate, aromatic sulfonic acids such as linear or branched alkylbenzene sulfonic acids, perchloric acid, nitric acid, and other mineral acids with appropriate equivalent conductances.

Cation eluent co-ions or suppression ions may include $C_1$–$C_7$ quaternary ammonium hydroxide which include alkyl and/or aryl groups, lithium hydroxide, sodium hydroxides, potassium hydroxide, and ammonium hydroxide, phosphonium hydroxides and/or sulfonium hydroxides.

The selection of suppression ion and co-ions are such that the suppressed salt formed in the effluent has a sufficiently low ionic conductance as to permit detection by the conductivity detector without undue background noise from the suppressed salt. For this purpose, for the analysis of a typical ionic species, this value may be on the order of 10 to 100 $\mu S$.

Eleunt and regenerant solvents may include alcohols, acetonitrile, dimethyl formamide, alkoxy ethanols such as 2-ethoxy ethanol, and methylethylketone. The solvents must be miscible in water.

Eluent surfactants may include non-ionic sufactants such as ethoxylated alcohols with 3–11 ethoxy groups and 9–15 carbon alkyl groups; alkylphenoxy polyethoxyethanols with 3–15 ethoxy groups and 3–11 carbon alkyl groups.

The suppression ions also form salts with the weak ionic species. This is highly advantageous for the analysis of many weak anions such as boric acid and weak cations such as triethanolimine which are poorly ionized in their respective acid and base forms, which form are the ones which must be analyzed in accordance with the prior art membrane suppression techniques. In contrast, the weak ionic species leave the membrane suppressor in the form of a salt with the suppression ions which have passed through the membrane. Such salts are more highly ionized than the acid or base form of the weak ionic species thus providing more effective detection of the ionic species by a conductivity detector.

ION-EXCHANGE RESIN BED SUPPRESSOR

In another embodiment of the IEC mode, an ion-exchange resin bed embodiment is substituted for the above membrane suppression technique but utilizing the same chromatographic separation and detection mode.

The exchangeable ions of the ion-exchange resin serve a similar function to the suppression ion set forth above. Firstly, they combine with the co-ion to form suppressed salts of lowered ion conductivity which is particularly important for detection of the ion by a conductivity detector. In addition, the exchangeable ions form salts with the weak ionic species of improved ionic conductance in comparison to the acid or base forms of such weak ions. Thus, the selection of suppression ions and co-ions are the same in this mode of the invention as in the above discussion with respect to the membrane embodiment.

The resin in the packed bed suppressor can be formed of an appropriate high capacity resin so that it can handle relatively large volumes of co-ions without allowing the same to reach the conductivity cell in highly ionized form. A suitable resin is a microporous styrene-divinyl benzene-based resin fully or partially cross-linked and with a medium diameter of 5 to 50 microns. The resin may be partially or fully sulfonated (for the analysis of cations) or aminated (for the analysis of cations). Sulfonation and amination may be performed by known techniques. Referring to anion analysis, the suppression ions such as TBA are passed through the column to functionalize the sulfonate group. In this instance, an appropriate acid may be utilized as the eluent for separation. In the suppressor column, the TBA ion is replaced by the hydrogen ion of the eluent. Thus, the suppressor resin becomes depleted and must either be regenerated by passage of a solution of TBA ions through the column or replaced with resin charged with TBA exchangeable ion. Since the fiber suppressor system is self regenerating and the suppressor packed bed is not, the former system would be the preferred one. However, there may be some applications where the packed beds suppressor resin may be particularly useful.

MOBILE PHASE ION EXCLUSION CHROMATOGRAPHY (MPIEC)

In this system, the principles of ion exclusion chromatography as set forth above are combined with certain principles of MPIC. In conventional MPIC, the ionic species to be separated are directed in a mobile phase, including mobile ion exchange site-forming compound, to a separating column comprising a neutral porous hydrophobic chromatographic medium, typically a resin bed. The separation occurs by conventional ion exchange of such ionic species and compounds. This is to be contrasted with the above IEC separation mode.

In the mode of MPIC, the separation medium comprises a porous hydrophobic chromatographic medium with essentially no permanently attached ion-exchange sites. The acid or base form of the co-ions function as ion-exchange site-forming compound and include a hydrophobic portion. Thus the co-ions form reversible adsorptive bonds with the chromatographic medium, preferably in the form of a packed bed of resin, to create ion-exchange sites thereon. The separation of the weak ions or cations in suppressed form is performed by selective temporary retention.

The system of the present invention is similar to IEC in that after the co-ions become attached to the resin bed, they serve as ion-exchange sites in a similar manner to the permanently attached ion-exchange sites of IEC set forth above. The advantages of MPIEC over IEC are similar to the analogous advantages of MPIC over conventional ion chromatography using resin with permanently attached ion-exchange sites. Such advantages are set forth in U.S. Pat. No. 4,265,634. They include the ability to optimize ionic separation over a large range of selectivities by eluent changes. In addition, large organic ions which are difficult to separate by conventional ion chromatography may be detected.

The principles of IEC are set forth above. The principles of using a mobile phase in the context of conventional ion chromatography are set forth in the aforementioned U.S. Pat. No. 4,265,634. Since the mode of separation is by ion exclusion, the co-ion which functions as the ion-exchange site-forming compound of the present invention is of the same positive or negative charge as is the ionic species to be detected. In contrast to MPIC as set forth in the aforementioned U.S. Pat. No. 4,265,634, in MPIEC the co-ion which serves as the ion-exchange site is of the same charge as the ionic species to be detected to permit ion exclusion, rather than ion exchange, to occur.

A suitable separation medium for MPIEC is the neutral macroporous resin used as the base material for the functionalized macroporous resin described above.

Referring to cation analysis, suitable ion-exchange site-forming compounds include (a) quaternary ammonium hydroxides which contain alkyl and/or aryl groups, (b) phosphonium, and (c) sulfonium groups. The co-ions of such compounds must be cationic and be of a type capable of forming reversible adsorptive bonds with the chromatographic bed. For this purpose, such co-ions typically include organic chains, specifically alkyl chains, of sufficient length for ready adsorption on the column, but not so long as to be too difficult to remove in a reasonable period of time. Also, the ion-exchange site-forming compound must be capable of being substantially precluded from passage through the walls of the suppressor fiber in ionic form. The counter ions of such co-ions are selected to pass through the membrane. Such counter-ions include carbonate, borate and hydroxide, all of which form weakly ionized acids or water in the suppressor column means.

The degree of adsorption of co-ion determines the column capacity which can be tailored to the desired retention time for a particular sample by the use of controlled amounts of an organic polar compound. For example, the degree of adsorption of TBAH increases significantly as the organic polar liquid (e.g. acetonitrile) content decreases.

For the analysis of anions, the ion-exchange site-forming compounds also must be of a type formed of a co-ion and a counter-ion capable of substantially being precluded from passage through the wall of the membrane suppressor device. Suitable co-ions for this purpose include: $C_1$–$C_{20}$ alkyl sulfuric acid, such as lauryl sulfuric acid, or alkyl and/or aryl sulfonic acids.

A preferred component of the mobile phase is a substantially non-ionic organic polar compound in an amount which serves to selectively reduce the retardation time of the ionic species in the separation bed in a controlled manner. Suitable polar liquids include lower alcohols, such as methanol and ethanol, acetonitrile, or any water miscible organic solvent.

In MPIEC, the co-ions must be suppressed in a manner analogous to the co-ion in the effluent of IEC using resin with permanently attached ion-exchange sites. The same modes of suppression may be employed, namely the preferred mode of membrane suppression and the other mode of the packed bed suppression. Since the co-ions used in both modes of chromatographic separation may be the same, the suppression techniques likewise may be the same using the same suppression ions. Thus reference should be made to the aforementioned modes of suppression which are suitable for MPIEC. Similarly, the conductivity detection may be performed in the same manner as set out above.

A further disclosure of the nature of the invention is provided by the following specific example of its practice.

EXAMPLE 1

This example illustrates formation of a membrane in the form of a fiber useful in the present invention. Tubing is supplied under the name Microline by Thermoplastic Scientifics, Inc. The base polymer is a copolymer of 91% ethylene and 9% vinyl acetate, cross-linked 40% to 65%. The average molecular weight is 190,000 with an average carbon number of 14,200 and a glass transition temperature of above 80° C. The dimensions of the tubing are 0.011 in. i.d. by 0.024 in. o.d. Styrene monomer is grafted onto the tubing by irradiation with gamma rays at a dose of 10,000 rad/hour for 120–200 hours.

A sulfonated anion fiber is formed by taking the above grafted fiber and swelling it in methylene chloride for 10 minutes. The tubing is functionalized by sulfonation by filling with a solution of 3% chlorosulfonic acid in methylene chloride and soaking at room temperature.

To form the aminated cation resin, vinylbenzyl chloride monomer is grafted instead of styrene monomer. The grafted tubing is swelled and then filled with a solution of 15% w/w methyldiethanolamine in methylene chloride. The tubing is aminated by reflexing at 45° C. for 40 hours at the ratio of 20 ml solution per foot of swelled grafted tubing.

EXAMPLE 2

This example illustrates the separation of organic acid by IEC and suppression using an anion fiber suppressor formed as set forth in Example 1.

The separator column is sold by Dionex Corporation of Sunnyvale, Calif. under part number 35330. The packed resin is a microporous styrene-divinyl benzene resin with 8% cross-linking, 8 micron bead size and is fully sulfonated. The column is 9 mm i.d. by 250 mm long.

The samples to be separated are the weak anions citrate (50 ppm), lactate (30 ppm) and acetate (50 ppm). The eluent is a strong acid 0.25 mM tridecafluoroheptanoic acid at an eluent flow rate of 1.0 ml per minute. After separation in the above column, the effluent is directed through a fiber suppressor device of the type described above. Regenerant, 10 mM TBAH is directed through the regenerant chamber at a flow rate of 2 ml/min. The conductivity is measured by a conductivity detector and three distinct peaks are formed in a chromatograph.

EXAMPLE 3

This example illustrates the separation of ammonium ion and quaternary ammonium compounds using MPIEC and a cation fiber suppressor.

In this example, the resin is neutral comprising macroporous ethylvinylbenzene-divinylbenzene with 57% cross-linking and 10 micron bead size packed into a 9 mm i.d. by 250 mm long column. The eluent is an aqueous solution comprising 1 mM phenyltrimethylammonium hydroxide at an eluent flow rate of 3 ml/min. The fiber suppressor column is an aminated cation fiber suppressor sold by Dionex Corporation of Sunnyvale, Calif. under part number 36179. The regenerant, 5 mM methane sulfonic acid, is flowed through the regenerant chamber at a flow rate of 3 ml/min. The sample comprises ammonium ion (at 100 ppm), tetrapentyl ammonium hydroxide (1,000 ppm), tetrapropyl ammonium hydroxide (500 ppm) and tetramethyl ammonium hydroxide (1,000 ppm). The conductivity is measured in a conductivity detector and four peaks are formed in a chromatogram, but with less distinct resolution than in Example 2.

EXAMPLE 4

This example illustrates the separation of sulfate and organic acids in the MPIEC mode.

The sample included sulfate ion, citrate ion, succinate ion, and acetate ion.

The separator column comprises a microporous ethylvinylbenzene-divinylbenzene resin at 6 micron bead size, with 57% cross-linking. The eluent is 0.25 mM tridecafluoroheptanoic acid at a flow rate of 1.5 ml/min. The fiber suppressor is a sulfonated polyethylene-vinyl acetate polymer formed as set forth in Example 1. The regenerate is 10 mM TBAH at a flow rate of 2 ml/min.

The conductivity is measured in a conductivity detector and the anions are separated into four distinct peaks in a chromatogram.

EXAMPLE 5

This example illustrates the separation of organic acid by MPIEC using suppression with a packed bed suppressor.

A sample includes an aqueous solution of citrate (50 ppm), succinate (50 ppm) and acetate (50 ppm).

The separator column comprises a macroporous surface sulfonated ethylvinylbenzene-divinylbenzene with 57% cross-linking. The eluent is 1 mM octane sulfonic acid at a flow rate of 2 ml/min.

The suppressor column is a packed bed anion suppressor packed in a column 9 mm i.d. by 100 mm long. The resin is formed by sulfonating 15-25 micron beads of microporous styrene-divinylbenzene resin and thereafter pumping TBAH over the resin to form the ion-exchange functional groups.

Detection is by a conductivity detector and a chromatogram is formed illustrating three distinct peaks.

What is claimed is:

1. A method of ion analysis and detection comprising:
   (a) eluting at least two weak ionic species to be determined past a chromatographic separation medium in an eluent to separate said ionic species, said ionic species being all of positive or negative charge and being in the form of weakly dissociated acids or bases or salts of weakly dissociated acids or bases, and, after separation, being in the form of acids or bases, said eluent comprising the hydronium or hydroxide form of co-ions of the same charge as said ionic species; and
   (b) containing the effluent from said separation medium with one side of an ion-exchange membrane having exchangeable ions of an opposite charge to said ionic species and being permeable to ions of the same charge as said exchangeable ions, and which resists permeation through the membrane of ions of opposite charge; and
   (c) simultaneously with step (b) contacting the opposite side of said membrane with a regenerant, said membrane forming a permselective partition between the regenerant and the effluent, said regenerant including salt-forming suppression ions of opposite charge to said ionic species and co-ions, said membrane being permeable to said suppression ions and to corresponding hydronium or hydroxide ions, said suppression ions being capable of forming suppressed salts with said co-ions of substantially lower equivalent conductance than the corresponding hydronium or hydroxide form of said co-ions, whereby hydronium or hydroxide ions extracted from the effluent at the ion-exchange sites of the membrane are diffused through the membrane into the regenerant and said suppression ions are diffused from the regenerant into the effluent to form the suppressed salt; and
   (d) then detecting said separated ionic species.

2. The method of claim 1 in which said membrane is continuously contacted by a flowing stream of fresh regenerant.

3. The method of claim 1 in which said ionic species and co-ions are anions, said suppression ions are cations, and said exchangeable ions are cationic.

4. The method of claim 1 in which said ionic species and co-ions are cations, said suppression ions are anions, and said exchangeable ions are anionic.

5. The method of claim 1 in which said suppression ions are selected from the group consisting of quaternary ammonium ions, carboxylates and sulfonates.

6. The method of claim 1 in which the separation step is performed by mobile phase ion chromatography in which said chromatographic separation medium comprises a porous hydrophobic chromatographic medium with essentially no permanently attached ion-exchange sites, and said acid or base form of co-ions function as ion-exchange site-forming compounds and include a hydrophobic portion, so that the co-ions form reversible adsorptive bonds with the chromatographic medium to create ion-exchange sites thereon, and the separation of the weak anions or cations in suppressed form is performed by selective temporary retention.

7. The method of claim 1, in which said detection is performed by a conductivity detector.

8. The method of claim 1, in which said chromatographic separation medium includes permanently attached ion-exchange sites with exchangeable ions of opposite charge to said weak ionic species, said chromatographic separation medium being in a form to substantially separate said weak ionic species by selective temporary retention.

9. A method of ion analysis and detection comprising:
   (a) eluting at least two weak ionic species to be determined past a chromatographic separation medium in an eluent to separate said ionic species, said ionic species being all of positive or negative charge and being in the form of weakly dissociated acids or bases or salts of weakly dissociated acids or bases, and, after separation, being in the form of acids or bases, said eluent comprising the hydronium or hydroxide form of co-ions of the same charge as said ionic species;
   (b) contacting the effluent from said separation medium with ion-exchange resin having ion-exchange sites with exchangeable ions of an opposite charge to said ionic species and to said co-ions and being capable of forming suppressed salts with said co-ions of substantially lower equivalent conductance than the corresponding hydronium or hydroxide form of said co-ions; and
   (c) detecting said separated ionic species after formation of said salts.

10. The method of claim 1 in which said ionic species and co-ions are anions, and said exchangeable ions are cations.

11. The method of claim 9 in which said ionic species and co-ions are cations, and said exchangeable ions are anions.

12. The method of claim 9 in which said exchangeable ions are selected from the group consisting of quaternary ammonium ions, carboxylates and sulfonates.

13. The method of claim 9 in which the separation step is performed by mobile phase ion chromatography in which said chromatographic separation medium comprises a porous hydrophobic chromatographic medium with essentially no permanently attached ion-exchange sites, and said hydronium or hydroxide form of co-ions function as ion-exchange site-forming compounds and include a hydrophobic portion, so that the co-ions form reversible adsorptive bonds with the chromatographic medium to create ion-exchange sites thereon, and the separation of the weak anions or cations in suppressed form is performed by selective temporary retention.

14. The method of claim 9 in which said detection is performed by a conductivity detector.

15. The method of claim 9 in which said chromatographic separation medium includes permanently attached ion-exchange sites with exchangeable ions of opposite charge to said weak ionic species, said chromatographic separation medium being in a form to substantially separate said weak ionic species by selective temporary retention.

16. Apparatus for the chromatographic separation and analysis of ionic species in an eluent including an electrolyte comprising:
(a) chromatographic separation means;
(b) means for supplying said eluent to said chromatographic separation means;
(c) suppression means communicating with said separation means for treating effluent eluting the separation means, said suppression means comprising a regenerant compartment, an effluent compartment and an ion-exchange membrane separating said compartments, said membrane being selectively permeable to ions of the same charge as the exchangeable ions of said membrane and being capable of transporting ions of a size greater than 7 angstroms between said regenerant compartment and effluent compartment, said membrane being in a form to convert electrolyte in the effluent to a weakly conducting form; and
(d) detector means in communication with said suppressor means for detecting the ionic species eluting therefrom.

17. The apparatus of claim 16 in which said detector means comprises a conductivity detector.

18. The apparatus of claim 16 in which the membrane comprises one or more hollow fibers.

* * * * *